United States Patent [19]
Sutton et al.

[11] Patent Number: 5,284,491
[45] Date of Patent: Feb. 8, 1994

[54] CARDIAC PACEMAKER WITH HYSTERESIS BEHAVIOR

[75] Inventors: Richard Sutton, London, England; Ivan Bourgeois, Verviers, Belgium

[73] Assignee: Medtronic, Inc., Minneapolis, Minn.

[21] Appl. No.: 842,818

[22] Filed: Feb. 27, 1992

[51] Int. Cl.$^5$ ............................................. A61N 1/00
[52] U.S. Cl. .................................................... 607/17
[58] Field of Search ................................. 128/419 PG

[56] References Cited

U.S. PATENT DOCUMENTS

| | | | |
|---|---|---|---|
| 3,661,157 | 5/1972 | Fyson et al. | 128/419 PG |
| 3,857,399 | 12/1974 | Zacouto | 128/419 PG |
| 3,921,642 | 11/1975 | Preston et al. | 128/419 PG |
| 4,169,480 | 10/1979 | Digloy et al. | 128/419 PG |
| 4,363,325 | 12/1982 | Roline et al. | 128/419 |
| 4,856,523 | 8/1989 | Sholder et al. | 128/419 |
| 4,972,834 | 11/1990 | Begemann et al. | 128/419 PG |

OTHER PUBLICATIONS

"Dual Chamber Pacing Aborts Vasovagal Syncope Induced by Head-Up 60° Tilt", Fitzpatrick et al. PACE, vol. 14, pp. 13-19.

*Primary Examiner*—Lee S. Cohen
*Assistant Examiner*—Marianne Parker
*Attorney, Agent, or Firm*—Harold R. Patton; Gregory P. Gadson

[57] ABSTRACT

A pacemaker having a hysteresis feature which permits intrinsic heart activity, controlled by the sinus node to resume optimally after pacing. The pacemaker has a programmable lower rate and upper rate, a programmable lower hysteresis rate (LRH) corresponding to a lower rate hysteresis interval (LRHI), and a programmable rate (IR) intermediate an upper pacing rate (UR) and a lower pacing rate (LR). A microprocessor measures the average rate of change $M_{AVG}$ in the intervals between consecutive ventricular depolarizations, and compares the last intrinsic escape interval $RR_N$ to the lower rate hysteresis interval (LRHI).

If the last intrinsic escape interval $RR_N$ is longer than the lower rate hysteresis interval (LRHI), and if the value of $M_{AVG}$ is greater than a first preselected value $SL_1$ but less than a second preselected value $SL_2$, the pacemaker stimulates at the lower rate hysteresis (LRH) and thereafter gradually increases the pacing rate up to the intermediate rate (IR). A time counter maintains a continuous pacing at the intermediate rate (IR) for a predefined period of time, and the pacing rate is gradually decreased toward the lower pacing rate (LR).

22 Claims, 7 Drawing Sheets

CARDIAC PACEMAKER WITH HYSTERESIS BEHAVIOR

BACKGROUND OF THE INVENTION

The present invention relates to cardiac pacemakers, and more specifically to a pacemaker having a selectable hysteresis feature which compensates for sinus node malfunction.

It is well known that natural heart activity, including the depolarization of the sinus node provides optimum hemodynamic performance. Atrial or ventricular stimulations induced by such devices as cardiac pacemakers, generally delay or inhibit natural heart activity by preventing the depolarization of the sinus node.

The hysteresis feature was developed to address this concern, by allowing the pacemaker to follow the sensed sinus node depolarization to a certain predetermined rate below the programmed lower rate of the pacemaker. As such, the escape interval in conventional demand pacemakers equipped with hysteresis feature, is longer than the lower rate interval, for enabling the patient's intrinsic rhythm to control the heart as long as the intrinsic rate is maintained above a predetermined minimum rate. However, in selected patients, these conventional pacemakers do not generally allow the natural heart activity to resume normally after pacing.

The following patents provide a brief historical background for the development and use of the hysteresis feature as it relates to cardiac pacing technology. U.S. Pat. No. 4,856,523, entitled "RATE-RESPONSIVE PACEMAKER WITH AUTOMATIC MODE SWITCHING AND/OR VARIABLE HYSTERESIS RATE," issued to Sholder et al, on Aug. 15, 1989, describes the inclusion of the hysteresis feature in a rate-responsive pacemaker, in an attempt to prevent competition between the pacemaker and the heart's SA node, when the anterograde conduction path is restored. The Sholder patent proposes to vary the hysteresis rate as a function of the pacemaker sensor rate, to a predetermined level upon sensing of the natural heart contraction during the escape interval, as illustrated in FIG. 3B and 4.

U.S. Pat. No. 4,363,325 entitled "MODE ADAPTIVE PACER," issued to Roline et al, on Dec. 14, 1982, and assigned to Medtronic, Inc., discloses a multiple-mode pacer which automatically switches from an atrial synchronous mode to a ventricular inhibited mode when the intrinsic atrial rate drops below a preset hysteresis rate. The Roline patent is incorporated herein by reference.

While the above cited patents and other publications and studies relating to the hysteresis feature have attempted with varying degrees of success to allow the patient's intrinsic rhythm to control, none was completely successful in causing the natural heart activity to resume optimally after pacing.

SUMMARY OF THE INVENTION

Briefly, the above and further objects and features of the present invention are realized by providing a new and improved pacemaker having a hysteresis feature which permits intrinsic heart activity, controlled by the sinus node to resume optimally after pacing.

The pacemaker has a programmable lower rate and upper rate, a programmable lower hysteresis rate (LRH) corresponding to a lower rate hysteresis interval (LRHI), and a programmable rate (IR) intermediate an upper pacing rate (UR) and a lower pacing rate (LR). A microprocessor measures the average rate of change in the intervals between consecutive ventricular depolarizations $M_{AVG}$, and compares the last intrinsic escape ($RR_N$) interval to the lower rate hysteresis interval (LRHI).

If the last intrinsic ventricular interval($RR_N$) will be longer than the lower rate hysteresis interval (LRHI), and if the value of $M_{AVG}$ is greater than a first preselected value $SL_1$ but less than a second preselected value $SL_2$, the pacemaker stimulates at the lower rate hysteresis (LRH) and thereafter gradually increases the pacing rate up to the intermediate rate (IR) while the pulse generator is in the demand mode. A time counter maintains a continuous pacing at the intermediate rate (IR) for a predefined period of time, and the pacing rate is gradually decreased down to the lower pacing rate (LR).

The accompanying Table I summarizes the features offered by the present invention, and correlates these features to FIGS. 2A through 6.

TABLE I

Figure 2A:
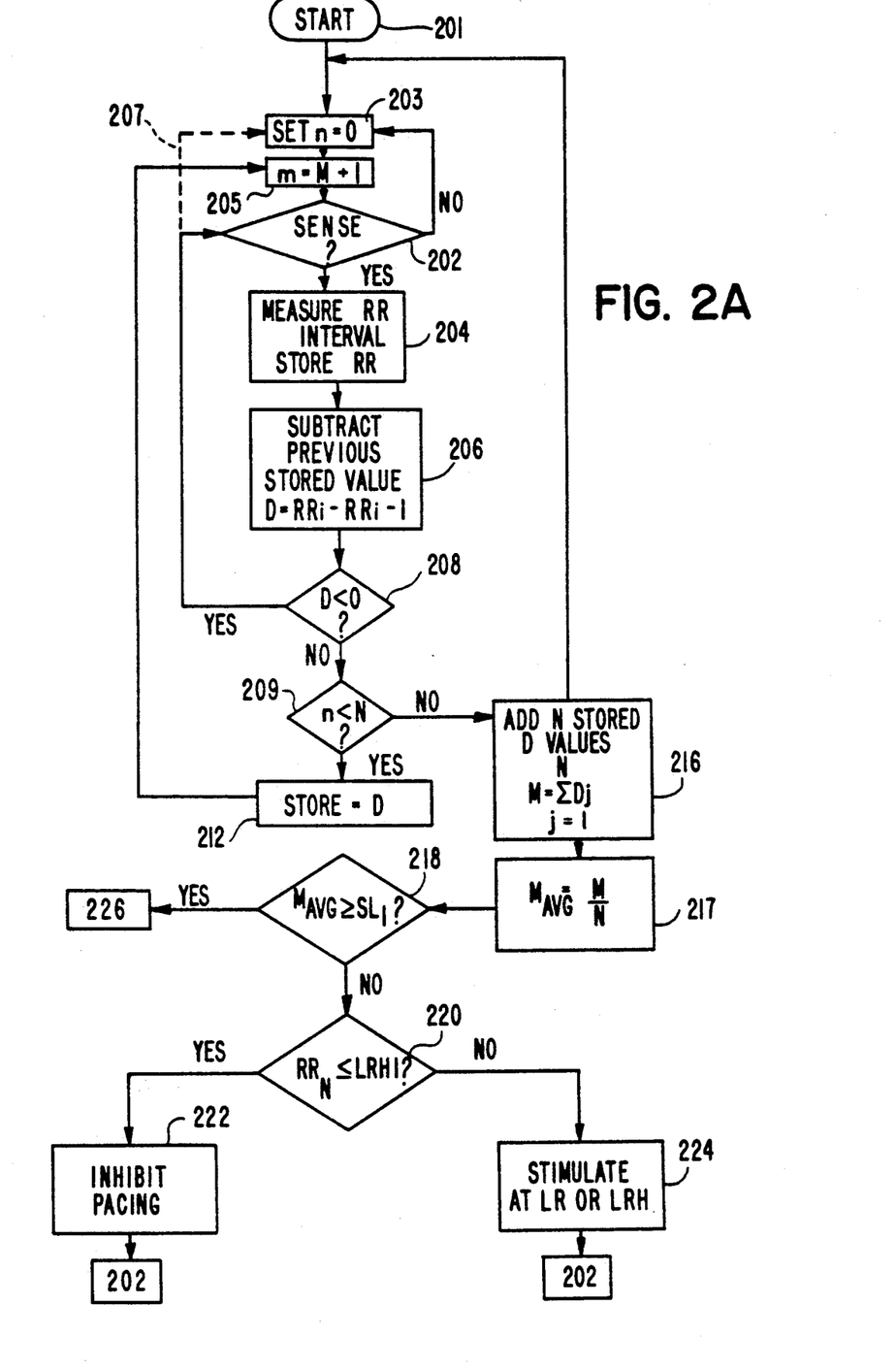
FIGS. 2A and 2B are flow charts of a simplified software program suitable for use in the pacemaker of FIG. 1.
Figure 2B:
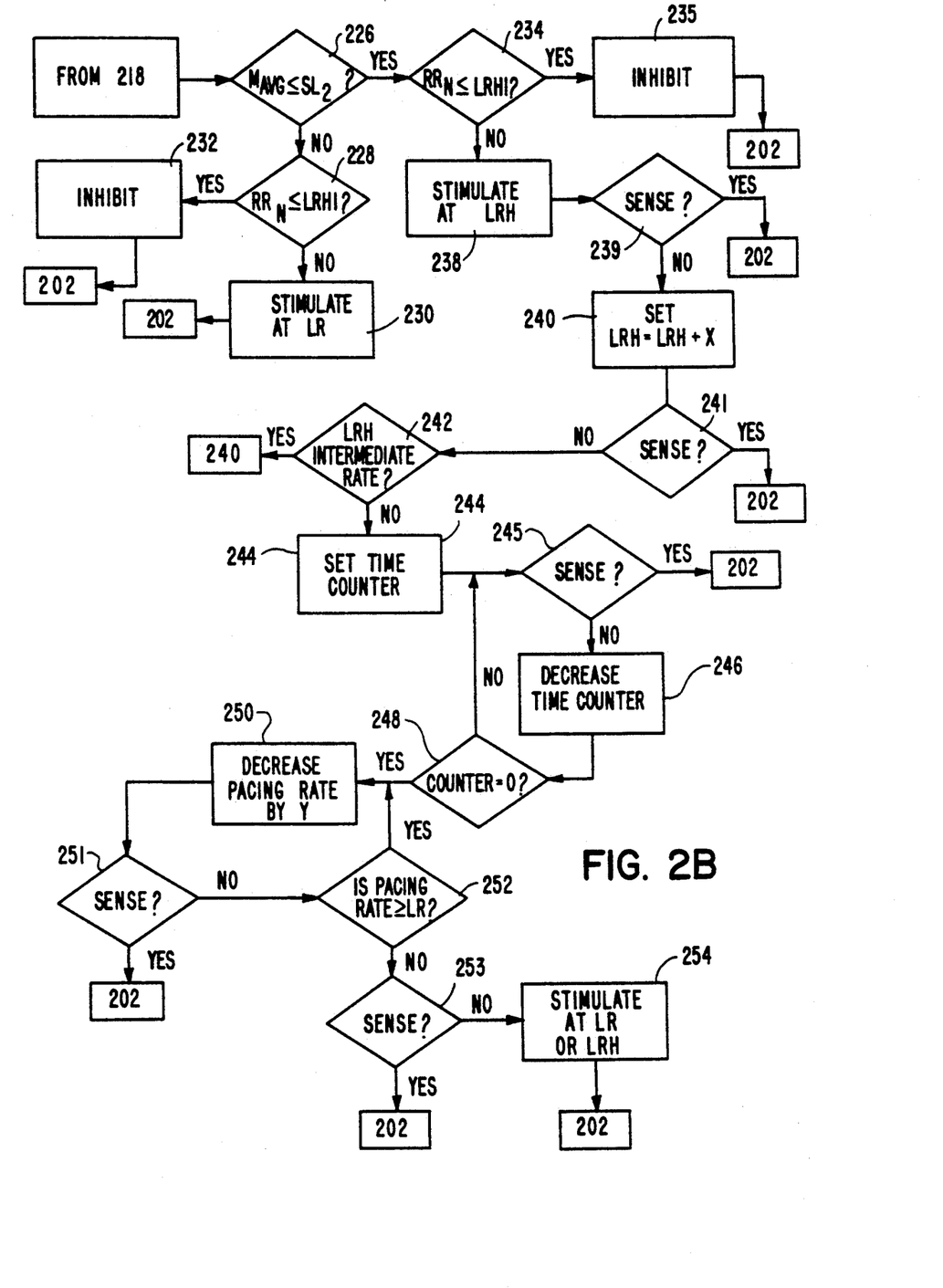
Figure 3:
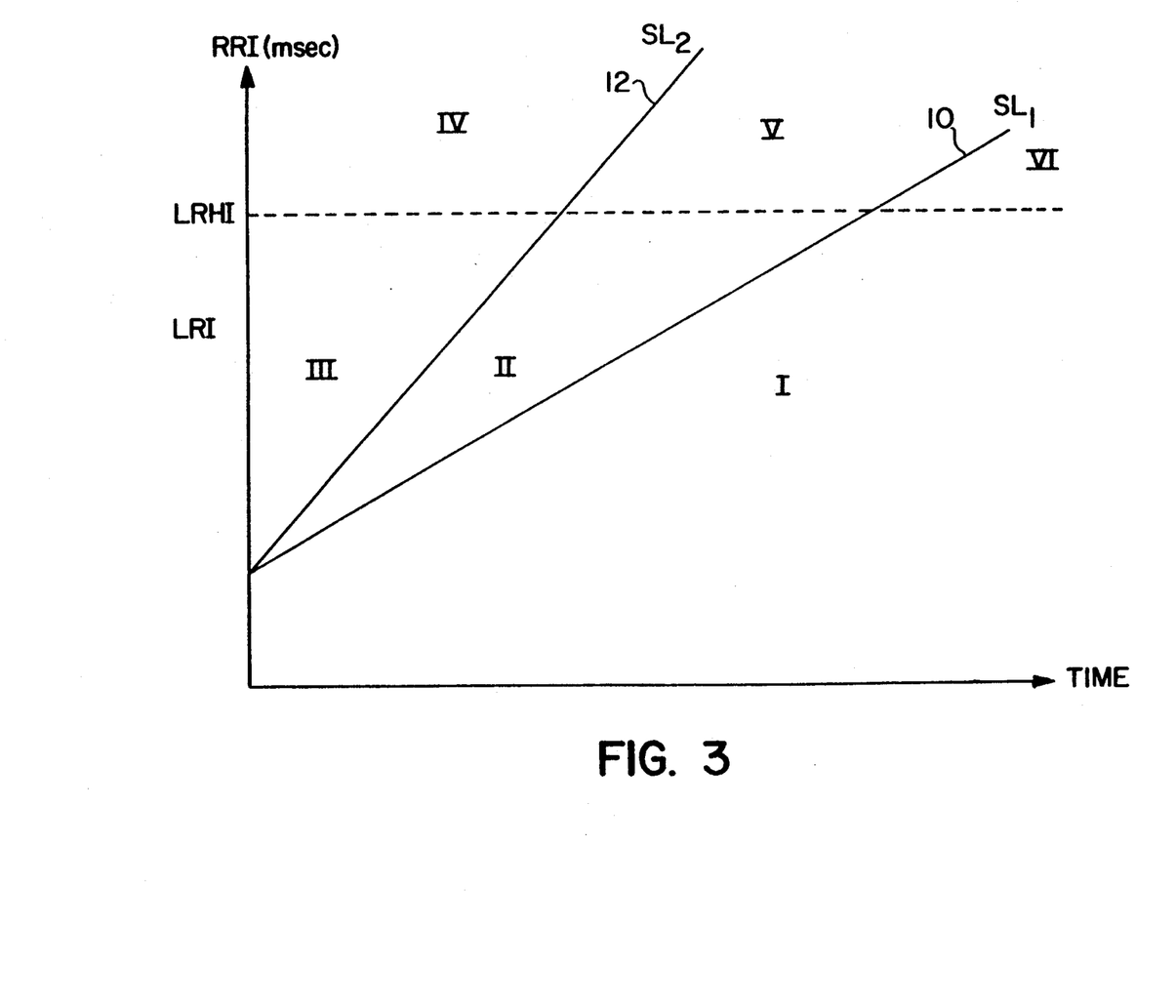
FIG. 3 is an illustration of two exemplary generally increasing limit functions $SL_1$ and $SL_2$ which determine the behavior of the pacemaker according to the software program of FIGS. 2A and 2B.
Figure 4:
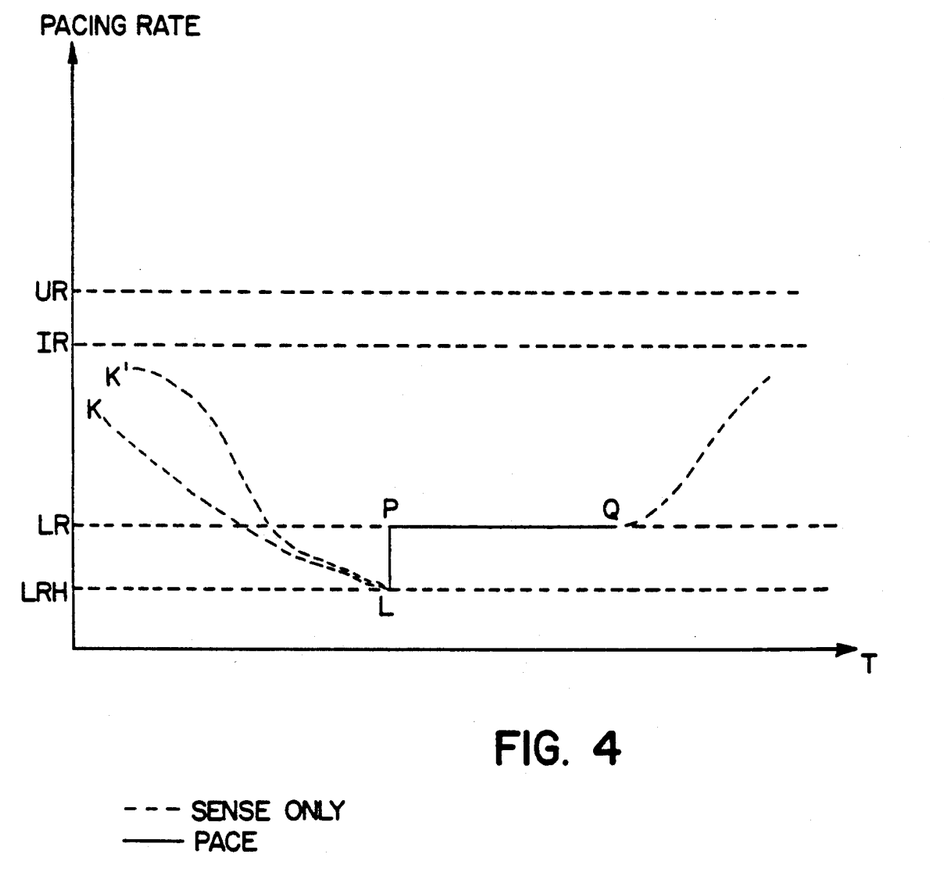
FIG. 4 is a response curve illustrating the variation of the pacing rate according to the present invention.
Figure 5:
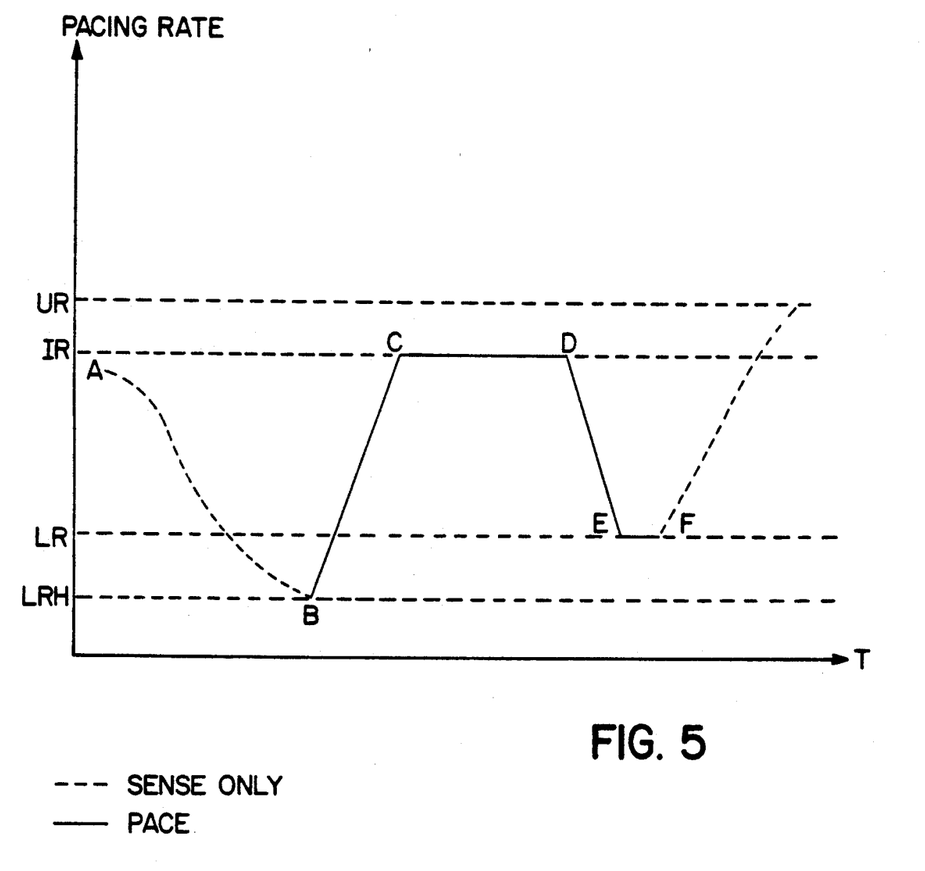
FIG. 5 is another response curve illustrating pacing rate variation according to the present invention.
Figure 6:
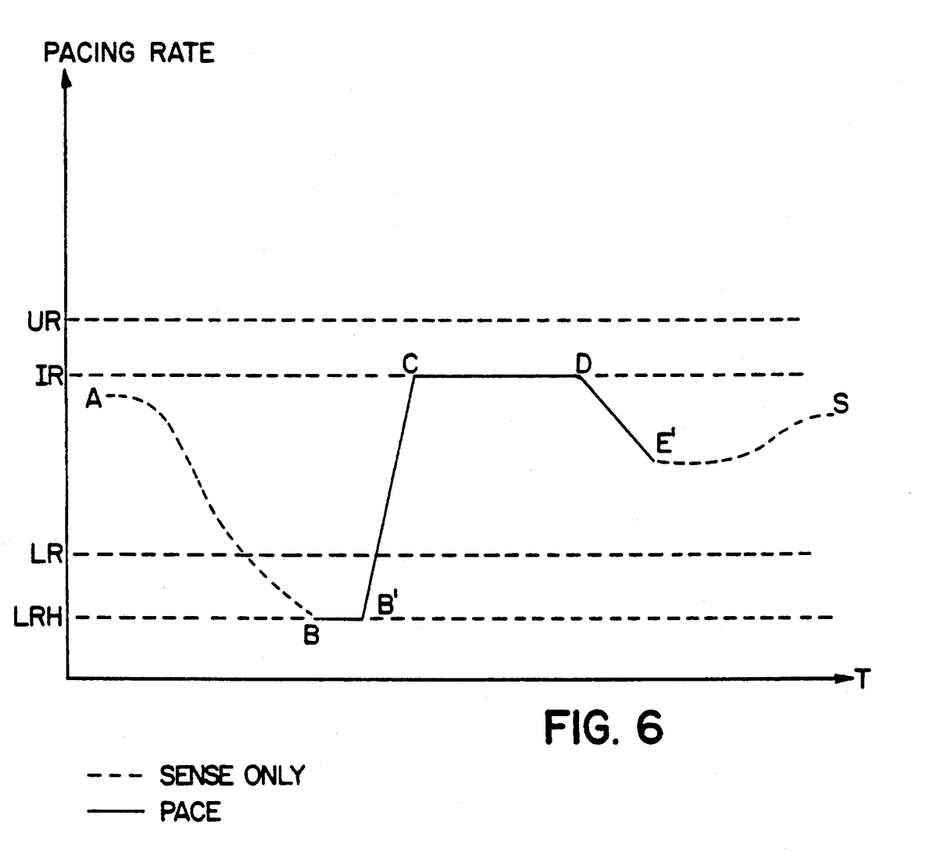
FIG. 6 is yet another response curve illustrating pacing rate variation according to the present invention.

| FIG. 2A (Step) | FIG. 2B (Step) | FIG. 3 (Region) | FIG. 4 (Curve) | FIG. 5 (Curve) | FIG. 6 (Curve) |
|---|---|---|---|---|---|
| 220, 222 | | I | KL | | |
| 220, 224 | | VI | LPQ | | |
| | 226, 228, 232 | III | K'L | | |
| | 226, 228, 230 | IV | LPQ | | |
| | 226, 234, 236 | II | | AB | AB |
| | 226, 234, 238–254 | V | | BCDEF | BB'CDE'R |

BRIEF DESCRIPTION OF THE DRAWINGS

The above and other options, features and advantages of the present invention will be more apparent from the following more particular description thereof, presented in conjunction with accompanying drawings, wherein.

DESCRIPTION OF THE PREFERRED EMBODIMENT

Figure 1:
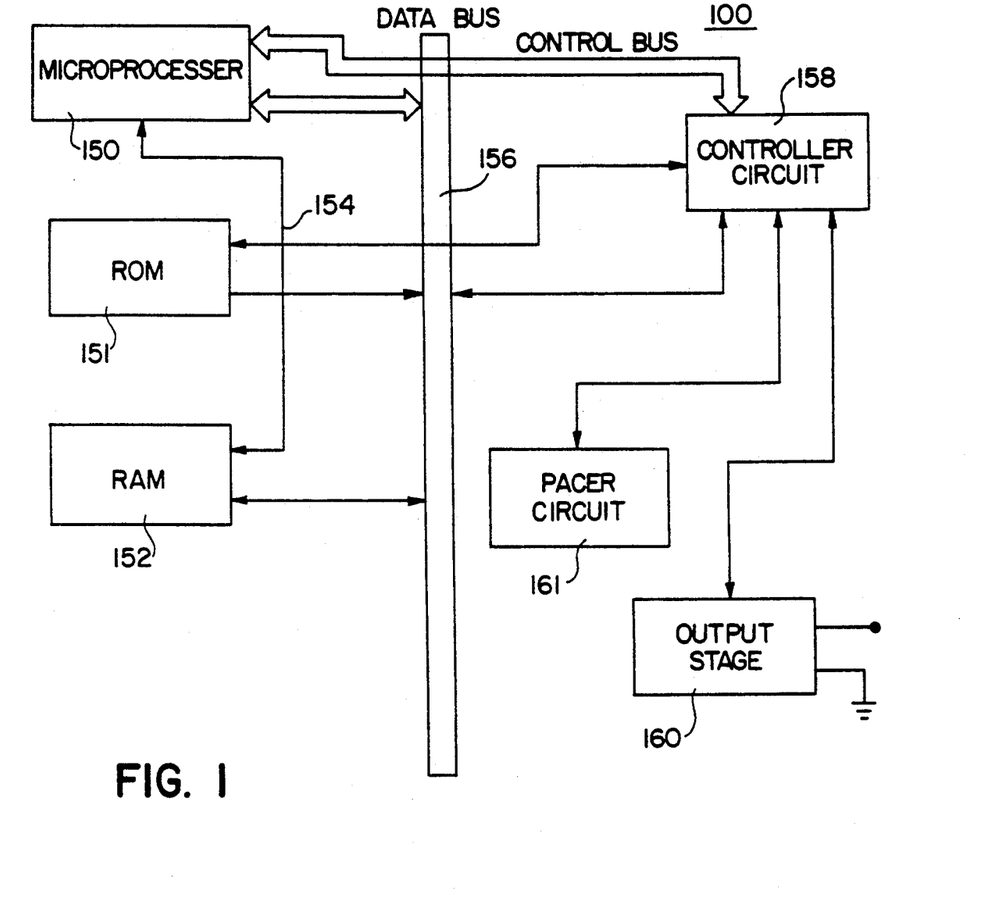
FIG. 1 is a block diagram showing the primary functional blocks of the pacemaker according to the present invention.

Referring now to the drawings and more particularly to FIG. 1 thereof, there is illustrated a block diagram of the components of the pacemaker 100 of the present invention. Block 150 illustrates a microprocessor chip, such as the CDP 1802 microprocessor made by RCA. The microprocessor 150 is connected to a ROM memory 151 and to a RAM memory 152 via a data bus 156. An address bus 154 interconnects the ROM memory 151, the RAM memory 152, and a controller circuit 158. The controller circuit 158, in turn, controls a pacer circuit 161 and a pacemaker output stage 160 for stimulating the heart. The pacemaker 100 could be used for single chamber or dual chamber pacing.

FIGS. 2A and 2B together illustrate the flow diagram of a program 200 which is stored in the ROM memory 151, and which is run once each cycle in the pacemaker 100. Alternatively, the program 200 could be stored in the RAM memory 152. The program 200 does not contain all the steps which are carried out by the microprocessor 150, but it includes those steps that illustrate the operation of the pacemaker 100 according to the present invention. Several variables of the software-controlled operations can be reprogrammed through the RAM memory 152.

Before proceeding with a more detailed explanation of the present invention, it would be helpful to review the following definitions:

"Intrinsic rhythm" or "intrinsic rate" of the heart is the rate at which the heart naturally beats on its own, without being stimulated by a pacemaker-provided stimulus.

"Hysteresis" means extension of the range of rates at which inhibition of the pacemaker pulses will occur. The base pacing interval is increased by the hysteresis interval. Thus, hysteresis provides a longer escape interval, thereby giving the heart an opportunity to beat on its own before the pacer provides stimulation pulses.

"Pacing Rate" is the rate at which the stimulation pulses are provided from the heart from the pacemaker.

Starting at step 201, the program 200 is initiated, and the intrinsic ventricular depolarizations are sensed at 202. While the program 200 uses ventricular events for carrying out the invention, it should be understood that atrial events can alternatively be used.

The program 200 measures, at step 204, the intrinsic escape interval, such as the RR interval between two successive sensed ventricular events, and calculates, at step 206, a parameter "D", as follows:

$$D = RR_i - RR_{i-1}, \quad (1)$$

where $RR_i$ is the RR interval which has been recently measured at step 204; and $RR_{i-1}$ is the RR interval preceding $RR_i$. It therefore follows that the parameter D is indicative of the rate of change of the RR interval.

In this respect, if D were found to have a positive value, it is an indication that the RR interval is increasing with time, and consequently the intrinsic rate of the heart is dropping. The reverse holds true where D has a negative value, indicating that the RR interval is decreasing and that the intrinsic rate is increasing. Additionally, the absolute value of D represents the rate of change of the intervals of the intrinsic ventricular depolarizations, which is also illustrated by the slope the curve AB in FIGS. 5 and 6, as it will be described later in greater detail.

If at step 208 the value of D is found to be negative, this value will not be used since it represents an increase in the intrinsic ventricular depolarization rate, and the above subroutine, including steps 202, 204, 206 and step 208, is repeated until a positive value of D is found. The dashed line 207 indicates that if the value of D is found to be negative, then the attending physician will have the option to either cause the software to set n=0, at step 203, or to restart at step 202. The preferred embodiment of the present invention relates principally to precipitous drops in heart rates, and consequently only positive values of D are added and stored at 212 by the random access memory RAM 152.

While the preferred embodiment includes adding only those positive values of D, it will become apparent to those skilled in the art that consecutive D values could alternatively be added. The feature of selecting between consecutive and positive D values is a programmable feature, and is selectable by the attending physician.

In order to detect and ascertain the occurrence of precipitous heart rate drops, the software 200 calculates the average rate of increase $M_{AVG}$ of a preselected number "N" of RR intervals. Preferably, $M_{AVG}$ is calculated over a predetermined period of time "T". If during that period T, the value of $M_{AVG}$ is less than a first limit function $SL_1$, then this is an indication that the intrinsic heart rate has not dropped rapidly enough to warrant the use of corrective measures, such as the activation of the hysteresis feature. If on the other hand, the value of $M_{AVG}$ reaches or exceeds the first limit $SL_1$, but is less than a second limit $SL_2$, the pacemaker is instructed to take appropriate measures, as will be described later in greater detail.

To achieve this function, the program 200 stores the calculated positive values of D, at step 212, and counts the number of events "n" indicative of a positive D value. When the count reaches a preprogrammed number "N" of stored beats or reaches the time period T, the program 200 calculates the sum "M" of the N stored values D, as follows:

$$M = \sum_{j=1}^{N} D_j, \quad (2)$$

where j is an integer that varies between 1 and N; and where N is the number of stored beats.

The value of M is then averaged at step 217 over the number of stored beats N, as follows:

$$M_{AVG} = \frac{M}{N} \quad (3)$$

In the preferred mode of the present invention the above parameters are assigned the following values:

N = 6 beats.

T = 15 seconds. It should, however, be understood that different values or ranges of values can alternatively be employed within the scope of the invention.

Digressing from the flow chart of FIG. 2A, and turning to FIG. 3, there is a shown lower limit function $SL_1$ and an upper limit function $SL_2$ which are identified by the numeral references 10 and 12, and which divide the quadrant into six regions: I, II, III, IV, V and VI. Each one of these regions will now be described in greater detail in relation to FIGS. 2A through 5. The horizontal coordinate axis represents time "t", and the vertical coordinate axis represents RR intervals "RRI".

As used in this specification, the LRI and LRHI parameters in the following context:

"LRI" means the Lower Rate Interval which corresponds to the lower pacing rate "LR" of the pacemaker, where LRI in milliseconds equals 60,000 divided by LR in beats per minute. LR is typically programmed to 70 beats per minute.

"LRHI" means the Lower Rate Hysteresis Interval that corresponds to the lower rate hysteresis "LRH" which is typically programmed to 50 beats per minute. LRHI in milliseconds equals 60,000 divided by LRH in beats per minute.

By comparing the average rate of change $M_{AVG}$ to the programmable limit functions $SL_1$ and $SL_2$, it would be possible to identify the region which corresponds to the mode of operation of the pacemaker 100. $SL_1$ and $SL_2$ are boundaries between regions defining distinctly different operation of the pacemaker 100. For clarity purposes, the six regions are defined as follows:

"Region I" is the portion of the quadrant defined by the lower limit function $SL_1$ and by the RRI and time axes. The pacemaker 100 operates in Region I whenever the value of $M_{AVG}$ is less than $SL_1$; and the last intrinsic ventricular escape interval $RR_N$ is shorter than the lower rate hysteresis interval LRHI. Pacing is inhibited in Region I, as illustrated by the curve KL in FIG. 4, and by step 222 of FIG. 2A. The curve KL shows the heart rate decreasing at a slow rate.

"Region II" is the portion of the quadrant defined by the limit functions $SL_1$ and $SL_2$, and by the lower rate hysteresis interval LRHI axis. The pacemaker 100 operates in Region II whenever the value of $M_{AVG}$ is greater than $SL_1$, but less than $SL_2$; and the last intrinsic ventricular escape interval $RR_N$ is shorter than LRHI. Pacing is inhibited in Region II, as illustrated by the curve AB in FIGS. 5 and 6, and by step 236 of FIG. 2B. The curve AB shows the heart rate decreasing at an intermediate rate.

"Region III" is the portion of the quadrant defined by the upper limit function $SL_2$, by the LRI axis and by the lower rate hysteresis interval LRHI axis. The pacemaker 100 operates in Region III whenever the value of $M_{AVG}$ is greater than $SL_2$; and the last intrinsic escape interval $RR_N$ is shorter than LRHI. Pacing is inhibited in Region III, as illustrated by the curve K'L in FIG. 4, and by the step 232 of FIG. 2B. The curve K'L shows the heart rate decreasing precipitously, as opposed to curve KL, which represents a more modest heart rate drop in Region I.

"Region IV" is the portion of the quadrant above the lower rate hysteresis interval LRHI axis, and defined by the RRI axis and by the upper limit function $SL_2$. The pacemaker 100 operates in Region IV whenever the value of $M_{AVG}$ is greater than $SL_2$; and the last intrinsic escape interval $RR_N$ will be longer than LRHI. As illustrated by the curve LPQ in FIG. 4, and by the step 230 of FIG. 2B, pacing is carried out at the lower rate LR. It should however be understood that pacing could be alternatively carried out at the lower rate hysteresis LRH.

"Region V" will be the portion of the quadrant above the lower rate hysteresis interval LRHI axis, between the two limit functions $SL_1$ and $SL_2$. The pacemaker 100 operates in Region V whenever the value of $M_{AVG}$ is less than $SL_2$ but greater than $SL_1$, and the last intrinsic escape interval $RR_N$ is longer than LRHI. As illustrated by the curves BCDEF and BB'CDE'R in FIGS. 5 and 6 respectively, and by steps 238 through 254 of FIG. 2B, pacing starts at the lower rate hysteresis rate LRH and gradually increases until the pacing rate reaches an intermediate pacing rate IR. Pacing at IR is maintained for a predetermined period of time, and is thereafter gradually reduced until it reaches the lower rate LR. Pacing is maintained at the lower rate until the intrinsic rate exceeds the pacemaker lower rate, as illustrated by the curve FG in FIG. 5. The pacemaker operation in Region V is triggered by an intermediate rate of decrease in the intrinsic hear rate.

"Region VI" is the portion of the quadrant defined by the lower limit function and by the lower limit function $SL_1$. The pacemaker 100 operates in Region VI whenever the value of $M_{AVG}$ is less than $SL_1$; and the last intrinsic ventricular escape interval $RR_N$ will be longer than the lower rate hysteresis interval LRHI. As illustrated by the curve LPQ in FIG. 4, and by the step 224 of FIG. 2A, pacing is carried out at the lower rate LR. It should however be understood that pacing could be alternatively carried out at the lower rate hysteresis LRH.

Returning now to FIG. 2A, the program 200 compares $M_{AVG}$ to $SL_1$ and step 218. If $M_{AVG}$ is less than $SL_1$, then a further determination is made at step 220 whether the last ventricular intrinsic escape interval $RR_N$ is less than or equal to LRHI. If it is, the pacemaker 100 operates in Region I, and pacing is inhibited, as indicated by step 222 in FIG. 2A and by the response curve KL in FIG. 4.

If the intrinsic escape interval ($RR_N$) is determined at step 220, to be equal to or tend to exceed LRHI, and if there is no sensed event at a shorter interval, while the pacemaker is still in the demand mode, the pacemaker 100 will operate in Region IV, and stimulation is carried out at the lower pacing rate LR, as illustrated by the curve LPQ in FIG. 4. The curves in FIGS. 4, 5 and 6 which are drawn in dashed lines indicate that pacing is inhibited, while the curves drawn in solid lines indicate that pacing is occurring.

Returning now to step 218 in the flow chart of FIG. 2A, if the program 200 determines that $M_{AVG}$ is greater than or equal to $SL_1$ then a further determination is made at step 226 whether $M_{AVG}$ is less than or equal to $SL_2$. If $M_{AVG}$ is found to be greater than $SL_2$ then the pacemaker 100 will operate in either Region III or Region IV. A further decision is made at step 228 whether the last intrinsic escape interval $RR_N$ is less than or equal to the lower rate hysteresis interval (LRHI).

If the program 200 determines that $RR_N$ is less than or equal to LRHI then the pacemaker 100 will operate in Region III, and as indicated by step 232 of FIG. 2B, and by the curve K'L in FIG. 4, pacing will be inhibited. If on the other hand, it is determined at step 228, that $RR_N$ is greater than LRHI, then the pacemaker 100 will operate in Region IV and as indicated by step 230 of FIG. 2B, and by the curve LPQ in FIG. 4, pacing is carried out at the lower pacing rate (LR).

The pacemaker 100 identifies and reacts to intermediate drops in the intrinsic heart rate, whenever $M_{AVG}$ is found to be intermediate the limit functions $SL_1$ and $SL_2$, as follows:

$$SL_1 \leq M_{AVG} \leq SL_2 \qquad (4)$$

In the above condition, the pacemaker is caused to pace at a gradually increasing pacing rate until it reaches a predetermined intermediate pacing rate (IR) which is lower than, or in certain circumstances, equal to, the upper pacing rate (UR). Demand pacing is maintained at the intermediate pacing rate (IR) for a predetermined period of time, and is thereafter reduced gradually.

With reference to FIG. 2B, the program 200 determines at step 234 whether the last intrinsic escape interval $RR_N$ is less than or equal to LRHI. If it is, then the pacemaker 100 will operate in Region II, and as indicated by step 236, and by the curve AB in FIGS. 5 and 6, pacing is inhibited.

If however, it is determined at step 234 that $RR_N$ will tend to be longer than LRHI, then the condition set forth in equation (6) above is satisfied, and the pacemaker 100 will operate in Region V, and will respond by pacing at the lower rate hysteresis (LRH) for a predetermined period of time or a preset number of beats, as illustrated by the dashed line BB' in FIG. 6, and by step 238 in FIG. 2B.

It should however be understood that the pacemaker 100 could alternatively bypass step 238 and start pacing along curve BC (FIG. 5), with one paced beat at the lower rate hysteresis (LRH). In this respect, pacing is started at point B (FIG. 5) and the pacing rate is incrementally increased until it reaches the intermediate rate (IR). The intermediate rate IR is programmable, and could be changed by the attending physician. The incremental increase in the pacing rate is illustrated by the curves BC in FIGS. 5 and 6. During this period, the pacemaker 100 is in the inhibited mode for single chamber pacemakers, or in the DDD or fully automated mode for dual chamber pacemakers.

The incremental increase of the pacing rate is achieved by steps 240 through 244, whereby the value of the pacing rate is incrementally increased by a center increment value X (step 240), and a determination is made at step 242 whether the pacing rate is less than or equal to IR. Once IR is reached, then, as indicated by step 244, a time counter is set to maintain the continuous pacing at that intermediate rate (IR) for a preselected programmable period of time, such as for five minutes. This continuous pacing at the intermediate rate is illustrated by curve CD in FIGS. 5 and 6. If during the execution of the subroutine 244 through 248, an intrinsic rhythm is sensed at 245, then the intrinsic rate prevails, and pacing is inhibited.

Once the counter time lapses, then, as illustrated by the curves DE and DE' in FIG. 5 and 6 respectively, the pacing rate is gradually decreased from the intermediate pacing rate (IR), toward the lower pacing rate (LR). This decrement is achieved by the subroutine 250-252, where the pacing rate is decreased by a counter decrement value Y until the pacing rate reaches the lower rate LR.

If decremental pacing is maintained until it reaches the lower rate LR, the pacemaker 100 starts pacing at that lower rate, as illustrated by the curve EF in FIG. 5, and the routine 200 is repeated. If an intrinsic rhythm is sensed at any time during the decremental change (curve DE') in the pacing rate, then the intrinsic rate prevails, and pacing is inhibited, as illustrated by the curve E'RS in FIG. 6. The subroutine 200 is thereafter repeated.

It is therefore clear that the new approach described in the present invention teaches away from the conventional hysteresis response feature. In the present invention, whenever an intermediate drop in the heart rate occurs and the hysteresis feature is activated, the natural heart rate resumes and is tracked until it reaches the hysteresis rate. Thereafter, the pacing rate is increased until the intermediate rate (IR) is reached. Pacing at that intermediate rate is maintained for a predetermined period of time, and thereafter allowed to gradually decay toward the lower rate.

It should become apparent to those skilled in the art after reviewing the present description, that the present invention can be made an integral part of single chamber and dual chamber pacemakers which operate in one or more of the programmed modes: SSI, SSIR, DDD, DDDR, DVI, DVIR, DDI and/or DDIR. The present hysteresis feature can be applied to the atrial and/or ventricular channels of a dual chamber pacemaker.

While the following ranges reflect exemplary values of IR, LR, UR, LRH, $SL_1$ and $SL_2$, it should be understood to those skilled in the art that other values and ranges can also be employed and/or programmed.

$100 \text{ bpm} \leq UR \leq 150 \text{ bpm}.$ $80 \text{ bpm} \leq IR \leq 100 \text{ bpm}.$ $60 \text{ bpm} \leq LR \leq 80 \text{ bpm}.$ $40 \text{ bpm} \leq LRH \leq 60 \text{ bpm}.$ $2\% \leq SL_1 \leq 10\%.$ $5\% \leq SL_2 \leq 20\%.$ $4 \text{ beats} \leq N \leq 16 \text{ beats}.$ While particular embodiments of the present invention have been disclosed, it is to be understood that various different modifications are possible and are contemplated within the scope and spirit of the specification, drawings, abstract, and appended claims.

What is claimed is:

1. In a pacemaker having a programmable lower rate and upper rate, a programmable lower rate hysteresis (LRH) corresponding to a lower rate hysteresis interval (LRHI), and a programmable intermediate pacing rate (IR) the improvement comprising:
   A. means for measuring rate of change $M_{AVG}$ of successive cardiac intrinsic escape intervals;
   B. means for comparing $M_{AVG}$ to a first predefined limit $SL_1$;
   C. means for comparing the last intrinsic escape interval to the lower rate hysteresis interval (LRHI); and
   D. means for stimulating a heart at the lower rate hysteresis (LRH) and for gradually incrementing a pacing rate until the pacing ratio reaches the intermediate pacing rate (IR) if the last intrinsic escape interval is longer than the lower rate hysteresis interval (LRHI) and if said $M_{AVG}$ is greater than $SL_1$.

2. The pacemaker according to claim 1 further comprising:
   A. time counter means for maintaining continuous pacing at the intermediate rate (IR) for a predefined period of time; and
   B. means for allowing gradual decay of the pacing rate after said selected period of time has lapsed.

3. The pacemaker according to claim 2, wherein said selected programmable time is set equal to five minutes.

4. The pacemaker according to claim 1, wherein said means for measuring the rate of change $M_{AVG}$ comprising:

A. means for measuring intervals between two successive ventricular depolarizations (RR intervals); and B. means for averaging the rate of change $M_{AVG}$ of said successive RR intervals.

5. The pacemaker according to claim 4, wherein said means for averaging the rate of change of said RR intervals comprises:

A. means for calculating a difference D between two successive RR intervals;
   B. means for comparing said difference D to a predetermined reference value;
   C. means for storing those values of D which are greater than said reference value;
   D. means for calculating a sum M of N stored values of D, wherein N is a predetermined positive integer; and
   E. means for setting $M_{AVG}$ equal to M/N.

6. The pacemaker according to claim 5, wherein said means for averaging $M_{AVG}$ comprising means for averaging the values of D greater than said reference value over a predefined period of time.

7. The pacemaker according to claim 6, wherein said reference value is zero, and wherein only positive values of D are stored and added.

8. The pacemaker according to claim 5, wherein N is set equal to six beats.

9. The pacemaker according to claim 4, further including means for comparing $M_{AVG}$ to a second predetermined limit $SL_2$ wherein $SL_2$ has a value greater than that of $SL_1$.

10. The pacemaker according to claim 9, wherein said means for stimulating gradually increments the pacing rate until the pacing rate reaches the intermediate pacing rate (IR), if the last intrinsic escape interval $RR_N$ is longer than LRHI, and if $M_{AVG}$ is greater than or equal to $SL_1$ but less than or equal to $SL_2$.

11. The pacemaker according to claim 9, further comprising means for inhibiting stimulation if $M_{AVG}$ is greater than $SL_2$, and if the $RR_N$ interval is less than or equal to LRHI.

12. The pacemaker according to claim 11, further comprising means for stimulating at the lower rate if $M_{AVG}$ is greater than $SL_2$, and if the RRN interval will be longer than LRHI.

13. The pacemaker according to claim 11, further comprising:
   A. means for inhibiting stimulation if $M_{AVG}$ is greater than $SL_2$, and if the $RR_N$ interval is less than or equal to LRH; and
   B. means for stimulating at the lower rate if $M_{AVG}$ is greater than $SL_2$, and if the $RR_N$ interval will be longer than LRHI.

14. The pacemaker according to claim 4, further including means for inhibiting stimulation if $M_{AVG}$ is less than $SL_1$, and if the last intrinsic escape interval $RR_N$ is less than or equal to LRHI.

15. The pacemaker according to claim 14, further comprising means for stimulating at the lower rate if $M_{AVG}$ is less than $SL_1$, and if the $RR_N$ interval will be greater than LRHI.

16. A method for pacing with a pacemaker having a programmable lower rate and upper rate, a programmable lower hysteresis rate (LRH) corresponding to a lower rate hysteresis interval (LRHI), and a programmable intermediate pacing rate (IR), the pacing method comprising the steps of:
   A. measuring a rate of change of $M_{AVG}$ of successive intrinsic escape intervals;
   B. comparing $M_{AVG}$ to a first predetermined limit $SL_1$;
   C. comparing a last intrinsic escape interval $RR_N$ to the lower rate hysteresis interval (LRHI); and
   D. stimulating at the lower rate hysteresis (LRH) and gradually incrementing a pacing rate until it reaches the intermediate pacing rate (IR) if the $RR_N$ interval will be longer than the lower rate hysteresis interval (LRHI) and if said $M_{AVG}$ is greater than $SL_1$.

17. The pacing method according to claim 16 further comprising the steps of:
   A. maintaining continuous pacing at the intermediate rate (IR) for a predefined period of time; and
   B. allowing gradual decay of the pacing rate after said selected period of time has lapsed.

18. The pacing method according to claim 17, wherein, said step of measuring the rate of change $M_{AVG}$ comprises:
   A. measuring intervals between two successive ventricular depolarizations (RR intervals); and
   B. averaging the rate of change $M_{AVG}$ of said successive RR intervals;

19. The pacing method according to claim 18, wherein said step of averaging the rate of change of said RR intervals comprises:
   A. calculating a difference D between two successive RR intervals;
   B. comparing the difference D to a predetermined reference value;
   C. storing those values of D which are greater than said reference value;
   D. calculating a sum M of N stored values of D, wherein N is a predetermined positive integer; and
   E. setting $M_{AVG}$ equal to M/N.

20. The pacing method according to claim 19, further comprising the step comparing $M_{AVG}$ to a second predetermined limit $SL_2$, wherein $SL_2$ has a value greater than that of $SL_1$.

21. The pacing method according to claim 20, wherein said step of stimulating comprises gradually incrementing the pacing rate until it reaches the intermediate pacing rate (IR), if the RRN interval will be longer than LRHI, and if $M_{AVG}$ is greater than or equal to $SL_1$ but less than or equal to $SL_2$.

22. The pacing method according to claim 18, further comprises:
   A. the step of inhibiting stimulation if $M_{AVG}$ is less than $SL_1$, and if the last sensed RR interval is less than or equal to LRHI;
   B. the step of stimulating at the lower rate if $M_{AVG}$ is less than $SL_1$, and if the $RR_N$ interval will be longer than LRHI;
   C. the step of inhibiting stimulation if $M_{AVG}$ is greater than $SL_2$, and if the $RR_N$ interval is less than or equal to LRHI; and
   D. the step of stimulating at the lower rate if $M_{AVG}$ is greater than $SL_2$, and if the $RR_N$ interval will be longer than LRHI.

* * * * *